(12) United States Patent
Arisawa et al.

(10) Patent No.: US 7,267,952 B2
(45) Date of Patent: Sep. 11, 2007

(54) METHOD OF EXTRACTING VIRUS GENES AND EXTRACTION APPARATUS

(75) Inventors: Junji Arisawa, Hokkaido (JP);
Kazuyuki Kimura, Hokkaido (JP);
Nobuo Katsuura, Kanagawa (JP);
Osamu Igarashi, Kanagawa (JP);
Atsushi Nakayama, Kanagawa (JP)

(73) Assignee: Nix, Inc., Kanagawa (JP)

( * ) Notice: Subject to any disclaimer, the term of this patent is extended or adjusted under 35 U.S.C. 154(b) by 616 days.

(21) Appl. No.: 10/469,737

(22) PCT Filed: Mar. 16, 2001

(86) PCT No.: PCT/JP01/02118

§ 371 (c)(1),
(2), (4) Date: Nov. 14, 2003

(87) PCT Pub. No.: WO02/070689

PCT Pub. Date: Sep. 12, 2002

(65) Prior Publication Data

US 2004/0072151 A1    Apr. 15, 2004

(30) Foreign Application Priority Data

Mar. 7, 2001 (JP) ............................. 2001-063834

(51) Int. Cl.
| C12Q 1/68 | (2006.01) |
| C12Q 1/70 | (2006.01) |
| C12N 15/10 | (2006.01) |
| C12N 7/02 | (2006.01) |
| C12M 1/12 | (2006.01) |
| C12M 1/42 | (2006.01) |

(52) U.S. Cl. .......................... 435/6; 536/25.4
(58) Field of Classification Search .................. None
See application file for complete search history.

(56) References Cited

U.S. PATENT DOCUMENTS 5,891,694 A    4/1999   Arisawa et al.

FOREIGN PATENT DOCUMENTS

| JP | 08-187086 | 7/1996 |
| JP | 2000-175682 | 6/2000 |

OTHER PUBLICATIONS

Birnboim, H.C. and J. Doly. A rapid alkaline extraction procedure for screening recombinant plasmid DNA. Nucleic Acids Res. 1979; 7:1513.*

Sugawara et al., "Extraction of the viral Gene by electrophoresis by using the metal coating hollow fiber membrane," The Institute of Electronics, vol. 100, No. 350, Oct. 2000, pp. 67-72.

(Continued)

Primary Examiner—Bruce R. Campell
Assistant Examiner—Stuart W. Snyder
(74) Attorney, Agent, or Firm—Steven J. Hultquist; Intellectual Property/Technology Law

(57) ABSTRACT

The present invention provides a method of extracting virus genes, which is excellent in quickness and convenience and can be automated, and this invention also provides an apparatus for such extraction of virus genes. A conductive hollow fiber membrane (module) 12 is immersed in a virus suspension 20 and thus viral particles suspended in the virus suspension 20 are captured in the conductive hollow fiber membrane (module) 12. The coating of the thus captured virus is lysed and the virus genes are released. Next, the virus genes are collected by subjecting the conductive hollow fiber membrane (module) 12 to at least one of an electrical treatment and a physical treatment.

10 Claims, 4 Drawing Sheets

OTHER PUBLICATIONS

Sugawara et al., "Extraction of the viral Gene by electrophoresis by using the metal coating hollow fiber membrane," Program of the 80th Hokkaido Medical Congress, Oct. 2000, pp. 16.

Sugawara et al., "Fundamental study on virus-control with the metal coating hollow fiber membrane," Hokkaido Institute of Technology, vol. 99, No. 458, Nov. 1999, pp. 17-22.

Kimura et al., "Application of the metal coating hollow fiber membrane to viral control," Memoirs of the Hokkaido Institute of Technology, vol. 28, Mar. 2000, pp. 1-7.

Sasaki et al., "Study of gene collection method by the metal coating hollow fiber membrane," Hokkaido Institute of Technology, vol. 99, No. 392, Oct. 1999, pp. 87-92.

* cited by examiner

METHOD OF EXTRACTING VIRUS GENES AND EXTRACTION APPARATUS

CROSS-REFERENCE TO RELATED APPLICATIONS

This application is filed under the provisions of 35 U.S.C. §371 and claims the priority of International Patent Application No. PCT/JP01/02118 filed 16 Mar. 2001, which in turn claims priority of Japanese Patent Application No. 2001-63834 filed 7 Mar. 2001.

BACKGROUND

The present invention relates to a method of extracting virus genes as well as an apparatus for such extraction. Particularly, this invention relates to a method and an apparatus for extracting virus genes by means of electrophoresis, using a conductive hollow fiber membrane.

Among virus infectious diseases, those caused by hepatitis viruses or human immuno-deficiency viruses (HIV) may lead to fatal diseases such as liver cirrhosis, liver cancer, or acquired immune deficiency syndrome (AIDS). Present diagnoses for these infectious diseases include an antibody assay, virus culture, and gene diagnosis. However, the antibody assay has problems in that it takes a very long period of time to confirm an antibody, and that before the antibody is confirmed, the patient may be given a false negative diagnosis.

The virus culture has some drawbacks, including: culturing methods are not established regarding some types of viruses; but even the viruses which can be cultured, have cultured cells which are different from each other; and it requires a considerable amount of time to culture these cells. On the other hand, the gene diagnosis requires many manual operations which are complicated. However, since the diagnosis can be conducted quickly, the gene diagnosis has been employed in many cases.

In the gene diagnosis, it is necessary to extract virus genes from a specimen, for which a chemical treatment is employed. However, the extraction procedures are complicated and require many manual op rations, which in fact have not been automated. When the number of viruses in a specimen is small, it is necessary to apply a pretreatment of virus enrichment by means of an ultracentrifuge for a long period of time, which is burdensome.

SUMMARY

The present invention aims to solve the above-described conventional problems. It is an object of this invention to provide a method of extracting virus genes, which is excellent in quickness and convenience and can be automated, and to also provide an apparatus for such virus gene extraction.

In order to achieve this object, this invention provides a method of extracting virus genes from a virus suspension, comprising the steps of: immersing a conductive hollow fiber membrane in the virus suspension and thereby capturing, in the conductive hollow fiber membrane, viruses suspended in the virus suspension; lysing the coating of the captured viruses and releasing the virus genes; and collecting the virus genes by subjecting, after the lysing step, the conductive hollow fiber membrane to at least one of an electrical treatment and a physical treatment.

The capturing step can include a step of aspirating the virus suspension via the conductive hollow fiber membrane.

The electrical treatment can include a step of conducting lectrophoresis by energizing the conductive hollow fiber membrane so that the conductive hollow fiber membrane becomes a cathode.

The physical treatment can include a step of forcing back, via the conductive hollow fiber membrane, the virus suspension that has been aspirated in the aspirating step.

Moreover, in the gene-collecting step, the electrical treatment and the physical treatment can be conducted at the same time.

Also, the coating of the viruses can be lysed chemically in the lysing step.

Furthermore, the electrophoresis step can be conducted by placing a semipermeable membrane between the cathode area and an anode area.

This invention also provides a virus gene extracting apparatus for extracting virus genes from a virus suspension, comprising: a conductive hollow fiber membrane immersed in the virus suspension in order to capture viruses in the virus suspension; a lysing liquid for lysing the coating of the viruses captured in the conductive hollow fiber membrane and releasing the virus genes; and a gene-collecting device which is capable of receiving the conductive hollow fiber membrane with the released virus genes captured therein, and which applies at least one of an electrical treatment and a physical treatment to the virus genes captured in the conductive hollow fiber membrane, thereby collecting the virus genes.

The virus gene extracting apparatus can further comprise a pump that is connected to the conductive hollow fiber membrane and is capable of aspirating the virus suspension via the conductive hollow fiber membrane.

The gene-collecting device can include an energizing device for energizing the conductive hollow fiber membrane so that the conducting hollow fiber membrane becomes a cathode.

Moreover, the gene-collecting device can include a mechanism for forcing back, via the conductive hollow fiber membrane, the virus suspension that has been aspirated by the pump.

Furthermore, a semipermeable membrane can be placed between the cathode area and an anode area.

DETAILED DESCRIPTION

A preferred embodiment of the method and apparatus for extracting virus genes according to this invention is described below with reference to the attached drawings.

Figure 1:
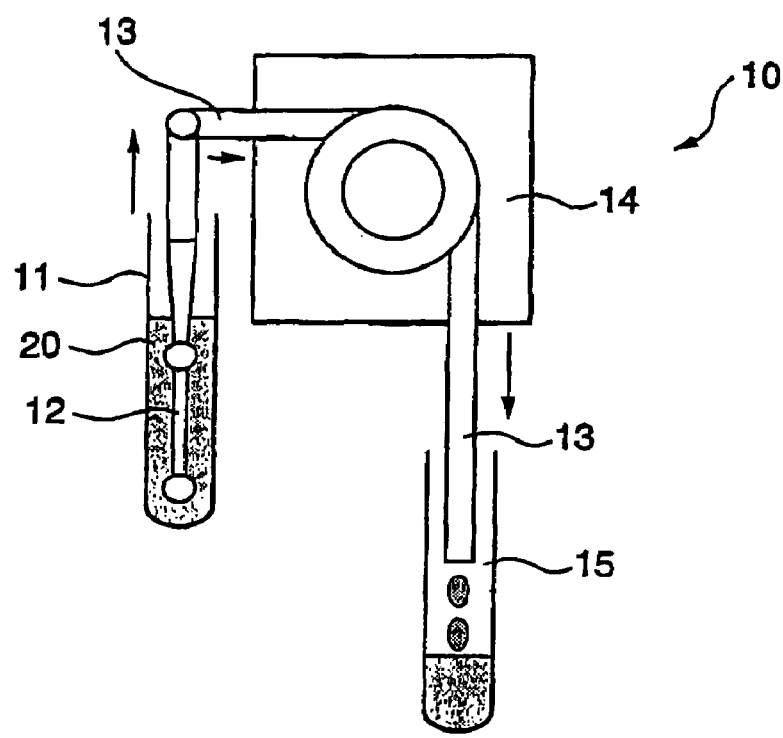
FIG. 1 is a schematic diagram of a capturing device for capturing viruses in a conductive hollow fiber membrane according to an embodiment of this invention.
Figure 2:
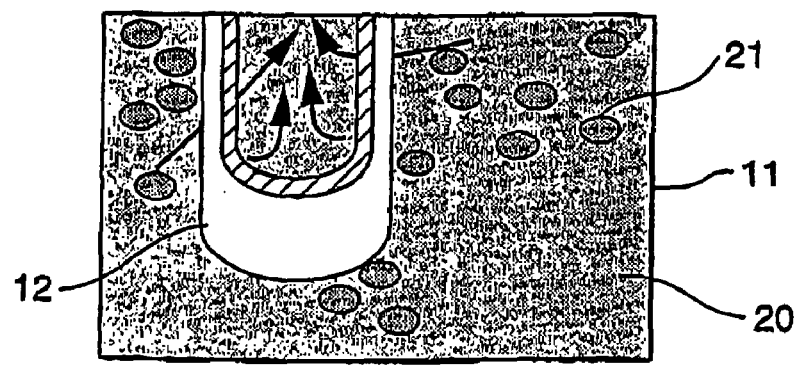
FIG. 2 is a fragmentary sectional view of the device of FIG. 1.
Figure 3:
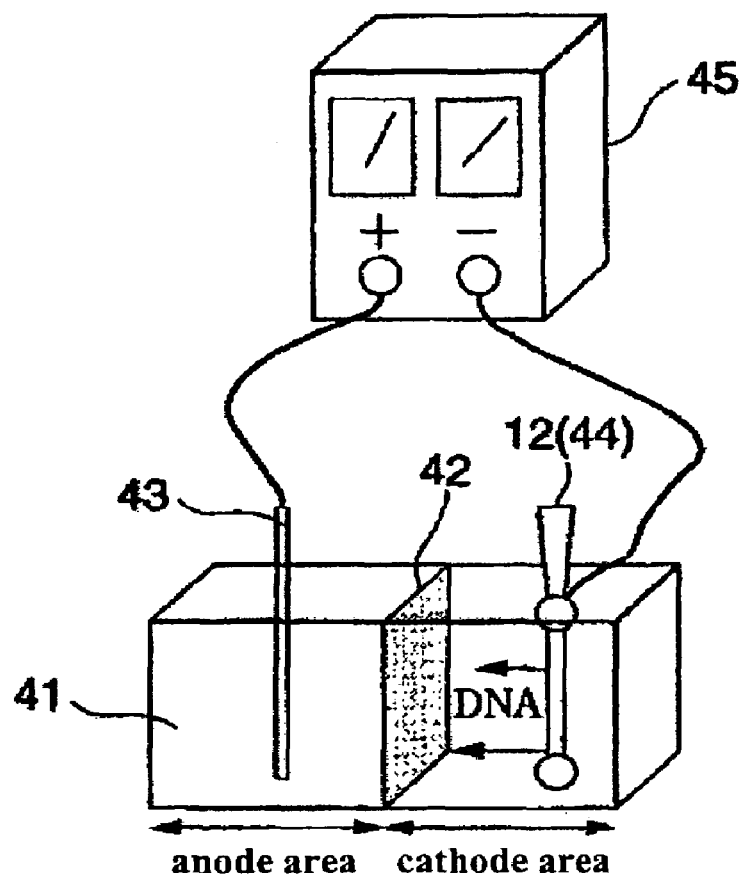
FIG. 3 is a schematic diagram of a gene-collecting device for collecting virus genes captured in the conductive hollow fiber membrane according to the embodiment of this invention.
Figure 4:
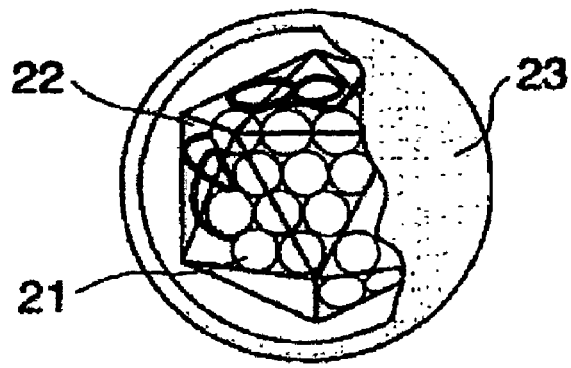
FIG. 4 is a diagrammatic illustration of the structure of a virus.

FIG. 1 is a schematic diagram of a capturing device for capturing viruses in a conductive hollow fiber membrane. FIG. 2 is a fragmentary sectional view of the device of FIG. 1. FIG. 3 is a schematic diagram of a gene-collecting device for collecting virus genes captured in the conductive hollow fiber membrane. FIG. 4 is a diagrammatic illustration of the structure of a virus.

The virus gene extracting apparatus of this invention comprises a capturing device 10 for capturing viruses in the conductive hollow fiber membrane, and a gene-collecting device for collecting the virus genes captured in the conductive hollow fiber membrane.

The capturing device 10 shown in FIGS. 1 and 2 comprises: a container 11 which contains a virus suspension 20; a conductive hollow fiber membrane module 12 for capturing viruses suspended in the virus suspension 20; a silicon tube 13 connected to the conductive hollow fiber membrane module 12; a pump 14 that is connected via the silicon tube 13 to the conductive hollow fiber membrane module 12 and is capable of aspirating the virus suspension 20 via the conductive hollow fiber membrane module 12; and a collecting container 15 for collecting the aspirated solution.

Concerning a virus used for this embodiment, herpes simplex virus type 1 (HSV) which has a relatively low risk and can be easily cultured is employed as a DNA virus similar to the hepatitis B virus (HBV).

As shown in FIG. 4, this virus 21 has a regular icosahedron nucleocapsid structure, which means that the arrangement of a capsid (protein coat) forms a regular icosahedron, which contains nucleic acids 22 (DNA) at its center. The outside of the structure is covered with an envelope 23 that is composed of lipid and glycoprotein. The size of this virus is approximately 150 nm to 200 nm in outside diameter.

In this embodiment, the liquid in which the viruses are suspended is diluted with a buffer solution for electrophoresis, and the obtained virus suspension 20 at a concentration of approximately $5\times10^3$ to $5\times10^6$ TCID$_{100}$/ml is used.

There is no particular limitation on the type of the container 11 as long as it is capable of containing the conductive hollow fiber membrane module 12 and the virus suspension 20. The details of the container 11, such as its shape or size, can be decided as appropriate according to, for example, the scale of the virus gene extraction.

The conductive hollow fiber membrane module 12 is structured in such a manner that a lead wire for energization is fixed with low melting solder at one end of a conductive hollow fiber membrane that has been cut to the length of approximately 2 cm, and the obtained conductive hollow fiber membrane is then connected to a solution aspirating nozzle, and the connection is fixed with epoxy resin. The other end of this conductive hollow fiber membrane module 12 is sealed with epoxy resin so that the solution can be aspirated via the conductive hollow fiber membrane. Because of this treatment, the effective length of the conductive hollow fiber membrane is approximately 1 cm.

In this embodiment, as the conductive hollow fiber membrane, a polypropylene hollow fiber membrane, which, for example, is used for simplified water purifiers in common use, and whose surface is coated with metal (such as gold [Au]) by electroless plating, is employed.

The shape of the conductive hollow fiber membrane is, for example, a cylinder (for example, approximately 1.8 mm in outside diameter and approximately 1.2 mm in inside diameter). Regarding the conductive hollow fibers, polypropylene fibers are coated with metal to the depth of several tens of μm from the outside surface of th membrane, so that the inner part of the polypropylen fibers which are not coated with metal is formed as a polypropylene layer, which is what the hollow fiber membrane originally is. The polypropylene layer and the metal layer have sponge-like pores (the pore sizes, for example, are approximately 0.1 μm). The value of resistance of this conductive hollow fiber membrane is approximately 0.2 Ω/cm to 1.0 Ω/cm.

The gene-collecting device as schematically shown in FIG. 3 comprises: an electrophoresis tank 41; a semipermeable membrane 42 to divide the Inside of the electrophoresis tank 41 into two areas; an anode 43 located in one of the areas of the electrophoresis tank 41 as divided by the semipermeable membrane 42; a cathode 44 located n the other area of the electrophoresis tan 41 as divided by the semipermeable membrane 42; an energizing device 45 connected to the anode 43 and the cathode 44; and a mechanism 46 for forcing back, via the conductive hollow fiber membrane module 12, the solution aspirated by the pump 14 in the capturing device 10.

As the anode 43, for example, a platinum wire can be used. On the other hand, the cathode 44 is composed of the conductive hollow fiber membrane module 12 in which the virus genes released by the above-described capturing device 10 are captured.

The mechanism for forcing back, via the conductive hollow fiber membrane module 12, the solution aspirated by the pump 14 in the capturing device 10 is made by connecting the silicon tube 13, the pump 14, and the collecting container 15 to the conductive hollow fiber membrane module 12. The mechanism is structured so as to force back the solution by operating the pump in reverse.

The virus gene extraction was conducted by the following method, using the above-described apparatus for extracting virus genes.

First, the conductive hollow fiber membrane module 12 which was connected via the silicon tube 13 to the pump (Perista pump) 14 was immersed in approximately 4 ml of the virus suspension 20 contained in the container 1. The virus suspension 20 was then aspirated at an average speed of approximately 0.6 ml/min. This operation caused the viruses suspended in the virus suspension 20 to be captured in the conductive hollow fiber membrane. The solution aspirated via the conductive hollow fiber membrane module 12 was collected in the collecting container in order to examine the enrichment effect on the virus in the conductive hollow fiber membrane. The aspiration was stopped when the volume of the remaining virus suspension 20 became 1 ml, that is, when 3 ml of the virus suspension 20 was aspirated, and the virus concentration was thereby terminated.

Subsequently, the conductive hollow fiber membrane module 12 in which the virus was captured was immersed in a virus lysing liquid for about 10 seconds, thereby chemically lysing the virus coating (i.e., the envelope 23 and the capsid). In this embodiment, a liquid mixture of 1% SDS and 10 mM NaOH was used as the virus lysing liquid. Accordingly, the virus genes (nucleic acids 22) captured in the conductive hollow fiber membrane module 12 were released.

The conductive hollow fiber membrane module 12, in which the thus released virus genes (nucleic acids 22) were captured, and a platinum wire were set in the electrophoresis tank 41 so that the conductive hollow fiber membrane module 12 would become the cathode 44 and the platinum wire would become the anode 43. The solution aspirated via the conductive hollow fiber membrane module 12 at the time of virus concentration was then forced back and, at the same time, an electric field was applied to the anode 43 and the cathode 44, thereby conducting electrophoresis. The electric field strength was either 2 V/cm or 4 V/cm, and the application time was selected from among 5 minutes, 10 minutes, and 15 minutes, As described above, in the electrophoresis tank 41, the semipermeable membrane 42 existed between the cathode area, in which the conductive hollow fiber membrane module 12 was located, and the anode area, in which the platinum wire was located. Therefore, the extracted virus genes (nucleic acids 22) existed only in the cathode area. After the electrophoresis, 5 μl out of approximately 1.5 ml of the solution in the cathode area was used, and 525 base pair (bp) regions of the genes contained in the 5-μl solution were amplified by the polymerase chain reaction (PCR) method. Subsequently, the amplified genes were fractioned by gel electrophoresis, thereby visually confirming whether the genes had been extracted or not.

Next, after the virus was concentrated and the virus coating was lysed in the same manner as described above, a basic examination was conducted to see whether it was possible to capture the virus genes from the conductive hollow fiber module 12 by conducting electrophoresis, using the conductive hollow fiber module 12 as the cathode 44.

Figure 5:
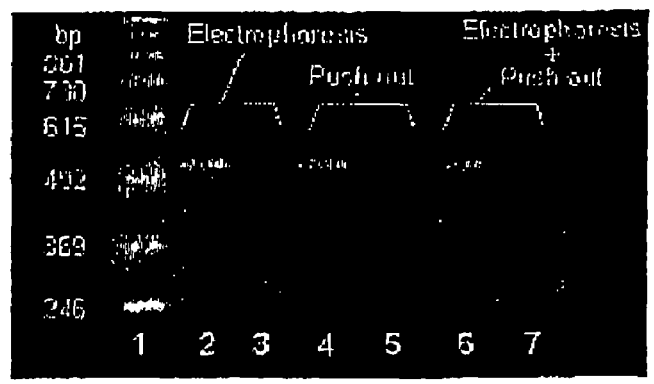
FIG. 5 shows the results of electrical and physical gene extraction according to the embodiment of this invention.

FIG. 5 (Lanes 2 and 3) indicates the results of conducting electrophoresis for 5 minutes with the electric field strength of 2 V/cm after th virus suspension 20 was aspirated in the amount of $5 \times 10^4$ virus genes and $5 \times 10^5$ virus genes. As shown in FIG. 5, when the virus suspension 20 with the virus concentration of $5 \times 10^5$ $TCID_{100}$/ml was aspirated, a gene band was recognized in a range from 492 bp and 615 bp. Since the 525 bp region of the virus genes was amplified by th PCR method, it was apparent that the recognized gene band was a virus gene fragment, Accordingly, it was shown that the virus genes concentrated in the conductive hollow fiber membrane could be extracted electrically by conducting electrophoresis, using the conductive hollow fiber membrane as the cathode electrode.

Subsequently, the virus genes were extracted physically and electrically by forcing back the solution, which had been aspirated via the conductive hollow fiber membrane module 12 at the time of virus concentration, from the inside of the conductive hollow fiber membrane module 12 toward the outside thereof and, at the same time, by applying an electric field to the anode 43 and the cathode 44.

Firstly, by forcing the solution from the inside of the conductive hollow fiber membrane module 12 toward the outside thereof, an examination was conducted to see whether the virus genes could be extracted physically from the conductive hollow fiber membrane module 12.

After the virus concentration and the lysing of the virus coating were conducted in the same manner as described above, the solution which had been aspirated via the conductive hollow fiber membrane module 12 at the time of virus concentration was forced out only in the amount (for example, approximately 1.5 ml) sufficient to be received in the cathode area of the electrophoresis tank 41 by using the pump 14, but without applying an electric field to the anode 43 or the cathode 44.

Only 5 μl of this forced-out solution was used for the PCR method in the same manner as described above, and an examination was conducted to see whether any virus genes were contained in the solution. FIG. 5 (Lanes 4 and 5) indicates this result. Referring to FIG. 5, just like in the case of the electrical extraction of the virus genes, the gene band was recognized only in the case where the virus concentration was $5 \times 10^5$ $TCID_{100}$/ml. Based on this result, it was confirmed that the virus genes concentrated in the conductive hollow fiber membrane could be extracted physically by forcing the solution out, using the pump 14.

Then, after the virus concentration and the lysing of the virus coating were conducted in the same manner as described above, the virus genes were extracted physically and electrically by using the pump 14 to force out the solution, which had been aspirated via the conductive hollow fiber membrane module 12 at the time of virus concentration, only in the amount (for example, approximately 1.5 ml) sufficient to be received in the cathode area of the electrophoresis tank 41 and, at the same time, by applying an electric field with the strength of 2 V/cm to the anode 43 and the cathode 44 for 5 minutes.

Subsequently, only 5 μl of this forced-out solution was used for the PCR method in the same manner as described above, and an examination was conducted to see whether any virus genes were contained in the solution. FIG. 5 (Lanes 6 and 7) indicates this result. Referring to FIG. 5, just like in the above-described case, the gene band was recognized only in the case where the virus concentration was $5 \times 10^5$ $TCID_{100}$/ml.

Accordingly, when either the electrical treatment or the physical treatment was applied to extract the virus genes, the virus genes in the amount of up to $5 \times 10^5$ $TCID_{100}$/ml could be xtracted in both cases. This means that both these treatments are effective extraction methods. Therefore, it is conceivable that a combination of these treatments may be more effective than only one of the treatments to extract the virus genes.

Next, the electric field application time and strength were examined at the time of gene virus extraction by means of electrophoresis. In this examination, the method of applying an electric field and, at the same time, forcing out the solution was employed.

As described above, it is apparent that the virus genes can be extracted with certainty from the conductive hollow fiber membrane, which has aspirated the virus suspension with the virus concentration of $5 \times 10^5$ $TCID_{100}$/ml, by applying the electric field with the strength of 2 V/cm for 5 minutes. Accordingly, the following examination was conducted with the electric field strength of 2 V/cm and the 5-minute application time as the reference.

Figure 6:
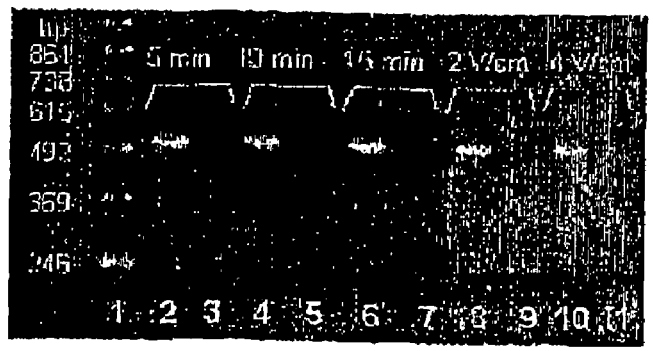
FIG. 6 shows the gene extraction results with regard to electric field application time and electric field strength according to the embodiment of this invention.

Firstly, the electric field strength was made constant (2 V/cm) and the application time was set to 5 minutes, 10 minutes, and 15 minutes, thereby conducting the virus gene extraction. FIG. 6 (Lanes 2 to 7) indicates the results. FIG. 6 (Lanes 2 to 7) indicates that even if the application time was changed from 5 minutes, to 10 minutes, and then to 15 minutes, the genes were only extracted up to $5 \times 10^5$ $TCID_{100}$/ml Subsequently, the application time was made constant (5 minutes) and the electric field strength of 2 V/cm and 4 V/cm was employed to extract the virus genes. FIG. 6 (Lanes 8 to 11) indicates the results. It is evident from FIG. 6 (Lanes 8 to 11) that even if the electric fi ld strength was changed from 2 V/cm to 4 V/cm, the genes were only extracted up to $5 \times 10^5$ $TCID_{100}$/ml.

The above-described examinations indicate that the conditions of electrophoresis in which the genes can be extracted most efficiently by the virus gene extracting method of this invention are to set the electric field strength to 2 V/cm and the application time to 5 minutes.

Next, in order to examine the concentration effect on the viruses in the conductive hollow fiber membrane, the virus concentrations were measured in the virus suspension and in the solution aspirated via the conductive hollow fiber membrane module. The concentration effect on the viruses in the conductive hollow fiber membrane was evaluated by comparing the amount of the virus contained in the solutions before and after the aspiration. The virus content is expressed by employing, as an index, tissue culture infectious dose 100% ($TCID_{100}$) which is commonly used for quantitative analysis of viruses. When the amount of active virus is large, the value of $TCID_{100}$ becomes large. On the other hand, when the amount of active virus is small, the value of $TCID_{100}$ becomes small. Table 1 indicates the results.

TABLE 1

|  | Virus Concentration ($TCID_{100}$) |
|---|---|
| Virus Suspension before Aspiration | $5 \times 10^6$ |
| Virus Suspension after Aspiration | <1 |

Table 1 indicates that the virus concentration of the virus suspension before the aspiration was $5 \times 10^6$ $TCID_{100}$/ml, while the virus concentration of the solution aspirated via the conductive hollow fiber membrane module was less than 1 virus gene/ml, Accordingly, it has been confirmed that all of the virus suspended in the virus suspension can be captured (or concentrated) in the conductive hollow fiber membrane by causing the virus suspension to pass through the conductive hollow fiber membrane.

Then, the virus suspension at the concentration of $5 \times 10^4$ $TCID_{100}$/ml, from which genes had not been extracted, was aspirated ten times more than the aspirated amount in the aforementioned examinations so that the amount of virus in the conductive hollow fiber membrane would become ten times more than that in the aforementioned examinations, thereby conducting an examination to see whether the virus genes could be extracted in the same manner as in the case of $5 \times 10^5$ $TCID_{100}$/ml. The aspirated amount of the virus suspension at the concentration of $5 \times 10^5$ $TCID_{100}$/ml was 1 ml, while the aspirated amount of the virus suspension at the concentration of $5 \times 10^4$ $TCID_{100}$/ml was 10 ml, which is ten times more than that of the $5 \times 10^5$ $TCID_{100}$/ml virus suspension. Moreover, the electric field strength was set to 2 V/cm and the application time was 5 minutes, FIG. 7 indicates the results.

Figure 7:
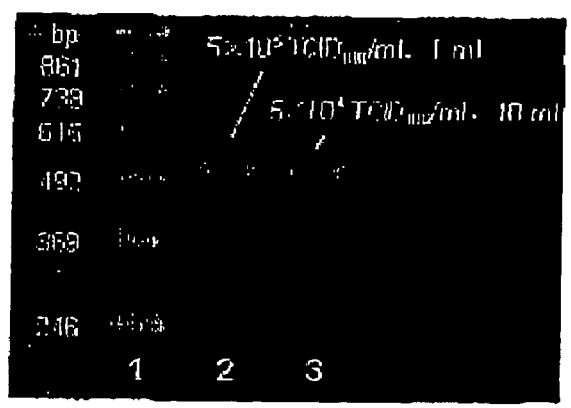
FIG. 7 shows the gene extraction results by utilizing the enrichment effect according to the embodiment of this invention.

While the aspirated amount of the virus suspension was 3 ml in the aforementioned experiment, the aspirated amount was reduced to 1 ml in this experiment. Ther fore, the absolute amount of the virus conc ntrated in the conductive hollow fiber membrane was reduced to on -third of that in the aforementioned experiment. However, in the case of $5 \times 10^5$ $TCID_{100}$/ml, as shown in FIG. 7 (Lane 2), the extraction of the virus genes was recognized, Subsequently, 10 ml of the virus suspension at the concentration of $5 \times 10^4$ $TCID_{100}$/ml, from which virus genes had not been extracted, was aspirated to extract the virus genes. As a result, as shown in FIG. 7 (Lane 3), the gene band was confirmed. This indicates that, just as in the case of aspiration of 1 ml virus suspension at the concentration of $5 \times 10^5$ $TCID_{100}$/ml, $5 \times 10^5$ virus genes were concentrated in the conductive hollow fiber membrane.

Concerning a conventional method of virus concentration, it is necessary to perform the concentration for a long period of time by using an ultracentrifuge. On the other hand, it is evident that virus concentration using the conductive hollow fiber membrane as per this invention is a very effective means.

In this embodiment, the concentration speed of the virus suspension was set to approximately 0.6 ml/min, but the concentration speed depends on the aspiration speed of the pump. Therefore, it is possible to control the concentration speed by means of the pump, and to further shorten the time.

As described above, only 5 µl out of the 1.5 ml solution in the cathod area, in which the gene extraction operation was conducted, was used for the PCR. In other words, only one-three hundredths (1/300) of the entire amount of the genes extracted from the conductive hollow fiber membrane exists in this 5 µl. Ther fore, an examination was conducted to see if the extraction sensitivity could be improved by newly adding the following gene concentration operation after the extraction of th virus genes.

Figure 8:
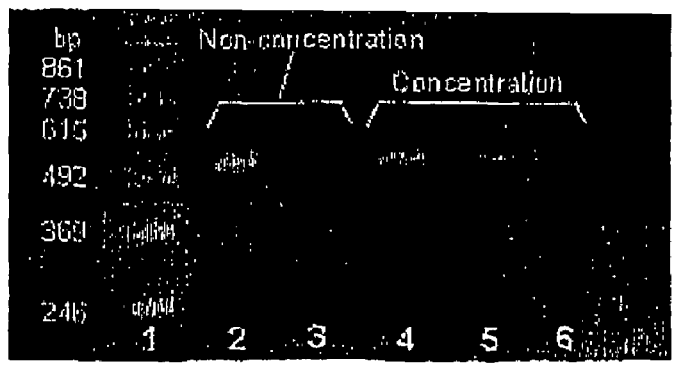
FIG. 8 shows the gene extraction results by using the conductive hollow fiber membrane and by limiting a virus concentration range according to the embodiment of this invention.

After the virus concentration and the lysing were conducted in the same manner as described above, the semipermeable membranes were placed in the electrophoresis tank to divide the tank into three areas, and the conductive hollow fiber membrane module was set in a central area of the three areas in the electrophoresis tank, and a platinum wire was set in either one of the remaining two areas. Then, the conductive hollow fiber membrane module was made to operate as the cathode, and the platinum wire was made to operate as the anode, and the electric field with the strength of 2 V/cm was applied for 5 minutes, thereby electrically extracting the genes from the conductive hollow fiber membrane module. However, since the buffer solution for electrophoresis (1.5 ml), to which 1% glycerin was added, was used in the central area, the physical extraction operation to force out the solution was not conducted. Subsequently, the conductive hollow fiber membrane module was moved to the other remaining area and the electric field with the strength of 2 V/cm was applied for 10 minutes, thereby causing the genes existing in the central area to be concentrated on the surface of the semipermeable membrane on the platinum wire side. Finally, a part of the semipermeable membrane was cut and placed in a PCR reactant solution, thereby amplifying the target genes. FIG. 8 shows the results. Referring to FIG. 8, the gene bands can be recognized in the case of $5 \times 10^5$ $TCID_{100}$/ml and also in the case of $5 \times 10^4$ $TCID_{100}$/ml from which no virus genes have been extracted.

As described above, this invention makes it possible to perform virus concentration by using the conductive hollow fiber membrane. Accordingly, the virus concentration that has conventionally required the ultracentrifugal op ration for a long period of time can be conducted for a short period of time (for example, for about 10 minutes with regard to the specimen amount of 6 ml). Moreover, this invention can provide a method of extracting virus genes, which is excellent in quickness and convenience and can be automated, and this invention can also provide the apparatus for such extraction of virus genes.

We claim:

1. A method of extracting virus genes from a virus suspension, comprising the steps of:
    immersing a conductive hollow fiber membrane in the virus suspension and thereby capturing, in the conductive hollow fiber membrane, viruses suspended in the virus suspension;
    lysing the coating of the captured viruses and releasing the virus genes; and collecting the virus genes by subjecting, after the lysing step, the conductive hollow fiber membrane to at least one of an electrical treatment and a physical treatment wherein said electrical treatment includes a step of conducting electrophoresis by energizing the conductive hollow fiber membrane so that the conductive hollow fiber membrane becomes a cathode, and wherein said physical treatment includes a step of forcing material that has previously passed through the conductive hollow fiber membrane, against the conductive hollow fiber membrane, in a reverse direction to its previous passage.

2. The method of extracting virus genes according to claim 1, wherein the capturing step includes a step of aspirating the virus suspension via the conductive hollow fiber membrane.

3. The method of extracting virus genes according to claim 2, wherein the material comprises the virus suspension that has been aspirated in the aspirating step.

4. The method of extracting virus genes according to claim 1, wherein the electrical treatment and the physical treatment are conducted at the same time.

5. The method of extracting virus genes according to claim 1, wherein the coating of the viruses is lysed chemically in the lysing step.

6. The method of extracting virus genes according to claim 1, wherein the electrophoresis step is conducted by placing a semipermeable membrane between the cathode area and an anode area.

7. A virus gene extracting apparatus for extracting virus genes from a virus suspension, comprising:
    a conductive hollow fiber membrane immersed in the virus suspension and capturing viruses in the virus suspension;
    a lysing liquid for lysing the coating of the viruses captured in the conductive hollow fiber membrane and releasing the virus genes; and a gene-collecting device which is capable of receiving the conductive hollow fiber member with the released virus genes captured therein, and which applies at least one of an electrical treatment and a physical treatment to the virus genes captured in the conductive hollow fiber membrane, thereby collecting the virus genes;

the gene-collecting device comprising at least one of (i) an energizing device for energizing the conductive hollow fiber membrane so that the conductive hollow fiber membrane becomes a cathode and (ii) a mechanism for forcing material that has previously passed through the conductive hollow fiber membrane, against the conductive hollow fiber membrane, in a reverse direction to its previous passage.

8. The virus gene extracting apparatus according to claim 7, further comprising a pump that is connected to the conductive hollow fiber membrane and is capable of aspirating the virus suspension via the conductive hollow fiber membrane.

9. The virus gene extracting apparatus according to claim 7, wherein the gene-collecting device includes a mechanism for forcing against the conductive hollow fiber membrane, the virus suspension that has been aspirated by the pump.

10. The virus gene extracting apparatus according to claim 9, wherein a semipermeable membrane is placed between the cathode area and the anode area of the gene-collecting device.

* * * * *

UNITED STATES PATENT AND TRADEMARK OFFICE
CERTIFICATE OF CORRECTION

PATENT NO.         : 7,267,952 B2
APPLICATION NO. : 10/469737
DATED                 : September 11, 2007
INVENTOR(S)       : Junji Arisawa et al.

It is certified that error appears in the above-identified patent and that said Letters Patent is hereby corrected as shown below:

Column 1, line 42: "manual op rations" should be -- manual operations --.

Column 4, line 13: "surface of th membrane" should be -- surface of the membrane --.

Column 4, line 14: "polypropylen fibers" should be -- polypropylene fibers --.

Column 7, line 2: "electric fi ld strength" should be -- electric field strength --.

Column 7, line 60: "Ther fore" should be -- Therefore --.

Column 7, line 62: "on -third" should be -- one-third --.

Column 7, line 65: "recognized, Subsequently" should be -- recognized. Subsequently --.

Column 8, line 20: "cathod" should be -- cathode --.

Column 8, line 24: "Ther fore" should be -- Therefore --.

Column 8, line 27: "th virus genes" should be -- the virus genes --.

Column 8, line 60: "op ration" should be -- operation --.

Signed and Sealed this

Fourteenth Day of October, 2008

JON W. DUDAS
*Director of the United States Patent and Trademark Office*